United States Patent
Rothaemel et al.

(10) Patent No.: US 9,724,620 B2
(45) Date of Patent: Aug. 8, 2017

(54) PROCESS AND PLANT FOR PRODUCING $C_2$-$C_4$ OLEFINS FROM METHANOL AND/OR DIMETHYL ETHER

(75) Inventors: Martin Rothaemel, Witten (DE); Henning Buchold, Hanau (DE); Harald Kömpel, Neu-Isenburg (DE); Andreas Glasmacher, Frankfurt (DE); Andreas Ochs, Friedrichsdorf (DE)

(73) Assignee: Lurgi GmbH, Frankfurt am Main (DE)

( * ) Notice: Subject to any disclaimer, the term of this patent is extended or adjusted under 35 U.S.C. 154(b) by 1786 days.

(21) Appl. No.: 12/089,823

(22) PCT Filed: Sep. 19, 2006

(86) PCT No.: PCT/EP2006/009076
§ 371 (c)(1),
(2), (4) Date: Sep. 8, 2008

(87) PCT Pub. No.: WO2007/042124
PCT Pub. Date: Apr. 19, 2007

(65) Prior Publication Data
US 2009/0124841 A1      May 14, 2009

(30) Foreign Application Priority Data
Oct. 13, 2005   (DE) ........................ 10 2005 048 931

(51) Int. Cl.
C07C 1/00      (2006.01)
B01D 3/14      (2006.01)
C07C 1/20      (2006.01)

(52) U.S. Cl.
CPC ................ B01D 3/143 (2013.01); C07C 1/20 (2013.01); C07C 2529/40 (2013.01); C10G 2300/807 (2013.01); C10G 2400/20 (2013.01); Y02P 30/42 (2015.11)

(58) Field of Classification Search
CPC ....... C07C 1/20; C07C 11/02; C07C 2529/40; B01D 3/143; C10G 2300/807; C10G 2400/20; Y02P 30/42
USPC ....... 585/315, 324, 408, 469, 609, 639, 640, 585/733, 638, 641, 642; 422/200; 208/302, 313
See application file for complete search history.

(56) References Cited

U.S. PATENT DOCUMENTS

| 4,542,252 | A  | * | 9/1985 | Graziani et al. | 585/640 |
| 4,849,573 | A  | * | 7/1989 | Kaeding | 585/640 |
| 5,643,442 | A  | * | 7/1997 | Sweet et al. | 208/302 |
| 2003/0080028 | A1 | * | 5/2003 | Tian et al. | 208/313 |
| 2003/0139635 | A1 | * | 7/2003 | Hack et al. | 585/609 |

FOREIGN PATENT DOCUMENTS

| DE | 3135618 | 3/1983 |
| DE | 10027159 | 12/2001 |
| DE | 10233975 | 2/2004 |
| EP | 0882692 | 12/1998 |

OTHER PUBLICATIONS

"Benzolgehalt in Kraftstoffen reduzieren", *CIT Plus, Filter/Trenntechnik* Oct. 2004, p. 45; also Aug. 19, 2004 version from Chemi.DE Information Service, with Aug. 19, 2004 English translation of Chemi.DE document, 2 pages.

"Pervaporation shows promise for separating benzene from aliphatics", *Chemical Engineering* Sep. 2004, 1 page.

Cretoiu, Lucia et al., "Sulfur Reduction With No Octane Loss—GT-DeSulf", *Presented at the ERTC 7th Annual Meeting*, Paris, France Nov. 2002.

Gentry, Joseph et al., "Extractive Distillation Applied", *Prepared for presentation at the 2003 AIChE SPrinq Meeting*, New Orleans, LA Apr. 2003, 14 pages.

* cited by examiner

*Primary Examiner* — Sharon Pregler
(74) *Attorney, Agent, or Firm* — Pauly, Devries Smith & Deffner, LLC

(57) ABSTRACT

In producing $C_2$-$C_4$ olefins, in particular propylene, from an educt mixture containing steam and oxygenates, such as methanol and/or dimethyl ether, the educt mixture is reacted in a reactor on a catalyst to a reaction mixture comprising low-molecular olefins and gasoline hydrocarbons, which in a first separating device is separated into a mixture rich in $C_{5-}$ olefins, a mixture rich in $C_{5+}$ gasoline hydrocarbons, and an aqueous phase. To increase the yield of propylene the mixture rich in $C_{5+}$ gasoline hydrocarbons is supplied to a second separating device, in which the aromatics contained in the mixture are separated. The residual stream largely free from aromatics is at least partly recirculated to the reactor.

18 Claims, 1 Drawing Sheet

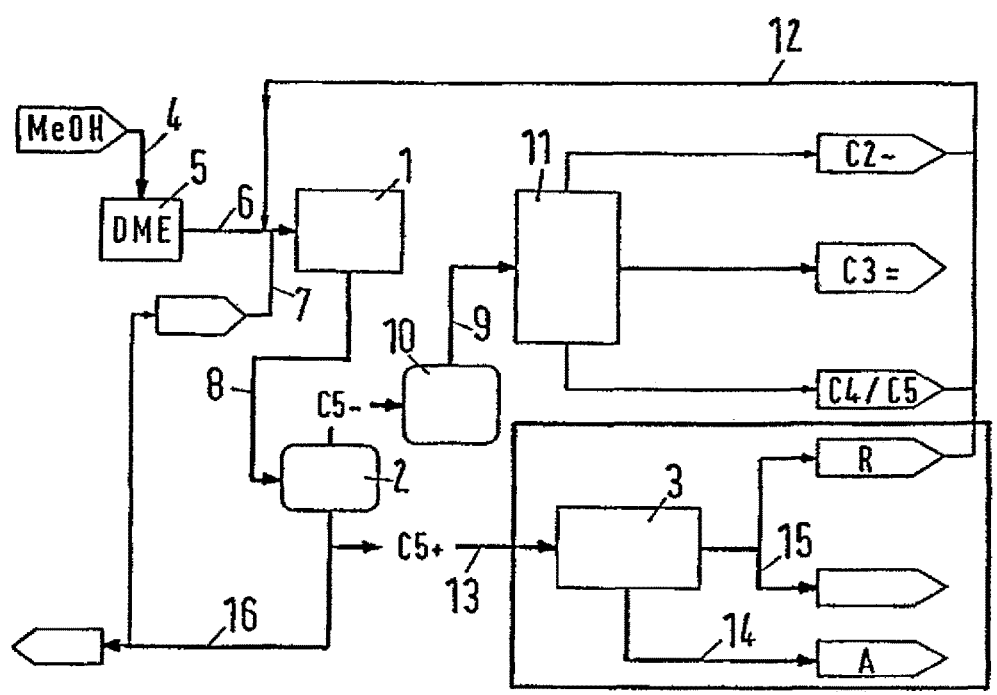

PROCESS AND PLANT FOR PRODUCING $C_2$-$C_4$ OLEFINS FROM METHANOL AND/OR DIMETHYL ETHER

CROSS-REFERENCE TO RELATED APPLICATIONS

This application is a national stage application under 35 U.S.C. 371 of International Patent Application Ser. No. PCT/EP2006/09076, entitled "Method and Arrangement for Producing $C_2$-$C_4$ Olefins from Methanol and/or Dimethyl Ether," filed Sep. 19, 2006, which claims priority from German Patent Application No. 10 2005 048 931.1, filed Oct. 13, 2005.

BACKGROUND

For producing low-molecular $C_2$-$C_4$ olefins, in particular propylene, from methanol and/or dimethyl ether, a multitude of processes are known to those skilled in the art, which are usually based on the reaction of an educt mixture containing steam as well as methanol vapor and/or dimethyl ether vapor on a form-selective zeolite catalyst.

DE 100 27 159 A1 describes, for instance, a process for producing propylene from methanol, in which first of all a vapor mixture containing dimethyl ether is produced from methanol vapor on a first catalyst, before said mixture is mixed with steam and is reacted in at least two series-connected shaft reactors with catalyst beds of form-selective zeolite to obtain a product mixture containing propylene. Subsequently, the product mixture is processed in a separating device comprising a plurality of distillation columns, so that there is obtained a fraction rich in propylene with a propylene content of at least 95 vol-%, a fraction containing low-molecular hydrocarbons, which is recirculated to the catalyst beds, and a fraction rich in gasoline hydrocarbons, which is removed from the process. What is, however, disadvantageous in this process is the low yield of propylene, based on the total carbon content of the educt mixture, which among other things is due to the fact that the fraction rich in gasoline hydrocarbons is removed from the process unused.

From EP 0 882 692 B1 there is known a process for producing $C_2$-$C_3$ olefins, in which a mixture of steam and methanol vapor and/or dimethyl ether vapor is reacted in a tubular reactor containing a zeolite catalyst at a temperature between 280 and 570° C. and a pressure between 0.1 and 0.9 bar to obtain a product mixture rich in olefins, which subsequently is separated in a separating device to obtain a $C_2$-$C_4$ olefin fraction with a propylene content of at least 40 wt-%, an aqueous fraction, a gaseous fraction, and a fraction containing $C_{5+}$ gasoline hydrocarbons. While the three first-mentioned fractions are withdrawn from the process, the product stream containing the $C_{5+}$ gasoline hydrocarbons is mixed with water, heated in a heater to a temperature of 380 to 700° C., and reacted to obtain $C_2$-$C_4$ olefins in a second reactor containing a zeolite catalyst, before the reaction products are recirculated to the separating device. The yields of $C_2$-$C_3$ olefins obtained with this process, although higher than in the process known from DE 100 27 159 A1, likewise are in need of improvement. In addition, this process is characterized by high costs, not least because of the isothermal procedure as well as the necessary vacuum operation in the tubular reactor.

In the known process, a liquid hydrocarbon product is obtained at the reactor outlet after the condensation apart from the gas mixture rich in propylene, which consists of olefins, paraffins, naphthenes and aromatics. To increase the yield, it would be conceivable in principle to recirculate this liquid product to the reactor, in order to selectively convert the olefins and naphthenes obtained into propylene. The aromatics, however, which likewise were recirculated necessarily and constitute the major part of the liquid product, react with the methanol supplied to the reactor as feed, for instance by alkylation of benzene to obtain toluene, of toluene to obtain xylenes, etc. Since as a result less methanol is available for the selective conversion of propylene, the achievable yield is reduced.

In the prior art, there are known various processes for separating aromatics (benzene, toluene, and xylenes) from hydrocarbon streams. While the liquid-liquid extraction for a long time has been the preferred process for recovering aromatics, an extractive distillation has been proposed quite recently, by means of which mixtures can be separated, whose components have only slightly different boiling points. Special solvents are used to increase the difference in volatility between the components to be separated. The extracting agent and the less volatile component flow to the bottom of the distillation column, where the extracted component is recovered by means of a further distillation. The non-extracted component is removed by distillation at the upper end of the extractive distillation column. For reducing sulfur in fuels, this GT DeSulf process has been presented for instance on the ERTC $7^{th}$ Annual Meeting, Paris, France, Nov. 18 to 20, 2002, by Lucia Cretoiu, Joseph C. Gentry, Sam Kumar and Randi Wright-Wytcherley "Sulfur Reduction With No Octane Loss—GT DeSulf" or on the 2003 AIChE Spring Meeting, New Orleans, USA, Apr. 1 to 2, 2003, by Joseph Gentry, Sam Kumar and Randi Wright-Wytcherley "Extractive Distillation Applied".

For reducing the benzene content of fuels, there was in addition proposed the separation by means of high-performance pervaporation membranes (cf. "Benzolgehalt in Kraftstoffen reduzieren", CIT plus 10/2004, page 45) or "Pervaporation shows promise for separating benzene from aliphatics", Chemical Engineering 9/2004).

SUMMARY

The present invention relates to a process for producing $C_2$-$C_4$ olefins, in particular propylene, from an educt mixture containing steam and oxygenates, such as methanol and/or dimethyl ether, in which the educt mixture is reacted in at least one reactor on a catalyst to obtain a reaction mixture comprising low-molecular olefins and gasoline hydrocarbons, which in a first separating device is separated into a mixture rich in $C_{5-}$ olefins, a mixture rich in $C_{5+}$ gasoline hydrocarbons, and an aqueous phase. The present invention furthermore relates to a plant suitable for performing the process.

DRAWINGS

FIG. 1 schematically shows a plant which is suitable for performing the process of the invention.

DETAILED DESCRIPTION

It is the object underlying the invention to increase the yield of $C_2$-$C_4$ olefins, in particular propylene, in a generic process.

This object is substantially solved with the invention by means of the features of claim 1, in that the mixture rich in $C_{5+}$ gasoline hydrocarbons is supplied to a second separating device, in which the aromatics contained in the mixture are largely separated and discharged as aromatics stream, and that the residual stream largely free from aromatics is at least partly recirculated to the at least one first reactor as recycling stream.

The known process can be improved by means of the invention in two ways. On the one hand, the liquid product liberated from aromatics now can completely be recirculated to the reactor, where the olefin and naphthene content can largely be converted to propylene, and hence the yield of the entire plant can be increased. On the other hand, there is additionally produced a valuable mixture of pure aromatics, which as compared to the original gasoline product has a distinctly higher value.

Since a 100% separation of the aromatics cannot be realized, the amount of aromatics in the recycling stream recirculated to the first reactor is an amount of less than 10 wt-%, preferably less than 5 wt-%, and in particular less than 1 wt-%, in accordance with the invention.

To control the concentration especially of the chemically inert paraffins in the circuit, part of the recycling stream largely free from aromatics, which is contained in the second separating device, is removed from the process in accordance with a development of the invention.

In accordance with the invention, the aromatics stream separated in the second separating device is separated into benzene, toluene and a xylene-isomer mixture in a further separating device, in order to increase the economic value of the aromatics mixture.

Preferably, the reactor constitutes a shaft reactor, tubular reactor, stationary fluidized-bed reactor or circulating fluidized-bed reactor. In the second case, the reactor preferably includes a plurality of axially arranged tubes, which for instance have a length between 1 m and 5 m as well as an inside diameter of 20 mm to 50 mm.

To achieve a rather high conversion of the educt mixture, the same is passed through two or more series-connected reactors, in accordance with a particular embodiment of the present invention. For this embodiment, in particular more than two, preferably four, series-connected shaft reactors each with a form-selective zeolite catalyst turned out to be particularly useful, part of the educt mixture from the prereactor being introduced into the first shaft reactor and the product mixture from the shaft reactor upstream of each further reactor together with a partial stream of the educt mixture from the prereactor being introduced into each further shaft reactor. Degrees of conversion just as good as that are obtained when as an alternative to the aforementioned embodiment the educt mixture is passed through only one reactor, in which at least two series-connected catalyst stages are provided. In this case, the individual catalyst stages preferably are arranged one below the other and are traversed by the educt mixture from the top to the bottom. Here as well, the educt mixture is distributed from the prereactor to the individual catalyst stages.

In principle, all zeolite catalysts known to those skilled in the art as suitable for converting methanol and/or dimethyl ether to $C_2$-$C_4$ olefins can be used in the at least one reactor, wherein alumosilicate zeolite of the pentasil type and particularly preferably ZSM-5 turned out to be particularly useful. For optimizing the yield, preferably at least one inert stream, particularly preferably steam, and at least one stream containing hydrocarbons, is supplied to the reactor or the first reactor stage.

In order to decrease the operating costs of the process, it is proposed in accordance with a development of the invention to perform the conversion in the at least one reactor adiabatically. Alternatively, an isothermal procedure can be provided, which as compared to the adiabatic procedure will, however, lead to higher process costs.

Good yields in the at least one reactor are obtained in particular, when an educt mixture with a weight ratio of water to methanol equivalent of 0.25:1 to 10:1 is supplied thereto. If the reactor comprises a plurality of catalyst stages, this ratio applies to the inlet of each catalyst stage. According to equation 2 with $CH_3OH \rightarrow CH_3-O-CH_3+H_2O$, one "methanol equivalent" corresponds to half a mole of dimethyl ether (DME). In addition, the educt mixture is preferably reacted in the reactor at a temperature of 300 to 600° C. and/or at a pressure of 0.5 to 5 bara.

For separating the reaction mixture withdrawn from the reactor, there can be used any separating device known to those skilled in the art, which is suitable for separating a mixture rich in $C_2$-$C_4$ olefins from a mixture rich in $C_{5+}$ gasoline hydrocarbons, for instance separating devices operating by distillation, by adsorption, thermally or by means of membranes. Particularly good results are obtained when the first separating device constitutes a cooling device and the reaction mixture withdrawn from the first reactor is cooled therein to a temperature of 10 to 80° C.

In accordance with a further preferred embodiment of the present invention, the mixture rich in $C_2$-$C_4$ olefins withdrawn from the first separating device is supplied to a third separating device, in which the aforementioned mixture is separated into a $C_4$-$C_5$ olefin stream and a $C_{3-}$ olefin stream. This provides for the recirculation of the $C_4$-$C_5$ olefin stream to the reactor, whereby the total yield of the process can further be increased. From the $C_{3-}$ olefin stream, propylene can for instance easily be recovered, for instance by distillation and with a high purity. Preferably, the olefins left upon separation of propylene from the $C_{3-}$ olefin stream are also recirculated to the reactor.

The invention also relates to a plant for producing $C_2$-$C_4$ olefins, in particular propylene, from an educt mixture containing steam and oxygenates, such as methanol and/or dimethyl ether, which plant is particularly useful for performing the process of the invention. In accordance with the invention, the plant comprises at least one catalytic reactor for converting the educt mixture into a reaction mixture comprising low-molecular olefins and gasoline hydrocarbons as well as a first separating device for separating the reaction mixture obtained in the reactor into a mixture rich in $C_{5-}$ olefins, a mixture rich in $C_{5+}$ gasoline hydrocarbons and an aqueous phase, as well as a second separating device which is adapted to separate the mixture rich in $C_{5+}$ gasoline hydrocarbons into a recycling stream substantially free from aromatics and an aromatics stream containing the separated aromatics, wherein a return conduit leads from the second separating device to the reactor.

In accordance with a preferred aspect of the invention, the second separating device is a membrane separating device. Alternatively, the second separating device can also include a distillation column in which preferably an extracting agent is added.

In accordance with a development of the invention it is proposed to provide a third separating device for separating the mixture rich in $C_{5-}$ olefins, which was withdrawn from the first separating device, into a $C_4$-$C_5$ olefin stream and a $C_{3-}$ olefin stream downstream of the first separating device, wherein the third separating device preferably includes at least one distillation column.

In accordance with a development of this invention, there is provided a return conduit leading from the third separating device to the reactor, in order to recirculate to the reactor the mixture rich in $C_4$-$C_5$ olefins, which was withdrawn from the third separating device.

Further features, advantages and possible applications of the invention can be taken from the following description of embodiments and from the drawing. All features described and/or illustrated in the drawing form the subject-matter of the invention per se or in any combination, independent of their inclusion in the claims or their back-reference.

The plant as shown in the FIGURE comprises a reactor 1 with a catalyst on the basis of form-selective zeolite, preferably an alumosilicate zeolite of the pentasil type and particularly preferably ZSM-5. The reactor 1 preferably constitutes a shaft reactor, tubular reactor, stationary fluidized-bed reactor or circulating fluidized-bed reactor. Furthermore, the plant comprises a first separating device 2 designed as cooler as well as a second separating device 3.

During operation of the plant, methanol supplied via a methanol supply conduit 4 is heated in a non-illustrated heat exchanger to a temperature of preferably 200 to 350° C. and is evaporated thereby, before the methanol vapor is at least partly reacted in the prereactor 5 on a suitable dehydrating catalyst, e.g alumina, to obtain dimethyl ether and water. Via a steam conduit 7, steam is supplied to the methanol/ dimethyl ether mixture withdrawn from the prereactor 5 via conduit 6, and the mixture thus obtained is introduced into the reactor 1. Preferably, the inlet temperature of the educt mixture into the reactor 1 is between 350 and 500° C., the weight ratio of water to methanol equivalent in the educt mixture is between 0.25:1 and 10:1, and the pressure in the reactor 1 is between 0.5 and 5.0 bara. In the vicinity of the catalyst of the reactor 1, the temperatures preferably lie in the range between 300 and 600° C.

As an alternative to the one-stage configuration of the reactor 1 as shown in the FIGURE, the same can also consist of two or more series-connected reaction stages, which can both constitute separately designed reactors and catalyst beds disposed one above the other in one reactor. In this case, the product from the prereactor 6 is distributed on the individual stages, whereas all other inlet streams are completely introduced into the first reaction stage. Furthermore, it is possible to exclusively use methanol or dimethyl ether in combination with steam as educt in the reactor 1 instead of a steam/methanol/dimethyl ether mixture.

Via conduit 8, the reaction mixture formed in the reactor 1 and chiefly consisting of $C_2$-$C_4$ olefins, $C_{5+}$ gasoline hydrocarbons and steam is withdrawn from the reactor 1 and supplied to the first separating device 2, in which the reaction mixture is cooled to a temperature between 10 and 80° C., so that a condensate rich in water, an organic liquid phase rich in $C_{5+}$ gasoline hydrocarbons, and a gaseous fraction rich in $C_{5-}$ olefins, which substantially consists of $C_2$-$C_4$ olefins, are obtained.

Upon passing through a compressor 10, the fraction rich in $C_{5-}$ olefins is supplied from the first separating device 2 via a conduit 9 to a third separating device 11, in which it is separated into a $C_4$-$C_5$ hydrocarbon stream, a $C_{2-}$ hydrocarbon stream and a propylene stream. It is also possible to first perform the separation of a $C_{3-}$ olefin stream and subsequently recover therefrom the propylene in a known way. The $C_4$-$C_5$ hydrocarbon stream and the $C_{2-}$ hydrocarbon stream are introduced into conduit 6 via a common or separate return conduit(s) 12 and together with the methanol/dimethyl ether mixture and the steam into the reactor 1.

Via conduit 13, the organic phase obtained in the first separating device 2, which substantially consists of $C_{5+}$ gasoline hydrocarbons, is introduced into the second separating device 3, in which the aromatics contained in the liquid product are virtually completely separated. For this purpose, the second separating device 3 is designed as membrane separating device or separates the aromatics in an extractive distillation by using special extracting agents. It is also possible to use the aforementioned processes in combination, possibly also in conjunction with a liquid-liquid distillation device. These processes are basically known to those skilled in the art. In so far, reference is made to the documents quoted in the introductory part of the description. By means of the second separating device 3, the aromatics are separated to such an extent that less than 5 wt-%, preferably less than 1 wt-% of aromatics are left in the residual stream. The separated aromatics stream A is discharged via conduit 14 and possibly further separated into benzene, toluene and a xylene-isomer mixture in a non-illustrated further separating device according to methods known to those skilled in the art.

The residual stream largely free from aromatics is recirculated to the reactor 1 as recycling stream R, for instance via return conduit 12.

To avoid a concentration in particular of the chemically inert paraffins in the circuit, part of the residual stream free from aromatics can be separated from the recycling stream R and be removed from the process via conduit 15.

The aqueous phase separated in the first separating device 2 can be discharged via conduit 16 and, upon conversion into steam, can possibly partly be recirculated to the process via conduit 7.

EXAMPLE

With an annual run time of 8000 h, a methanol charge of 208.3 t/h leads to a feed stream of 1.66 mio t/a. As the conversion of methanol necessarily involves the release of water, the percentage of the product yields relates to the so-called "$CH_2$" content (from the pseudoreaction $CH_3OH \rightarrow "CH_2" + H_2O$). For the "$CH_2$" content, the feed stream is 91.2 t/h (730 kt/a).

A comparison of the product distribution of the conventional process (MTP), as it is described for instance in EP 0 882 692 B1, with the process of the invention (MTP+), has resulted in the following product streams for the above-mentioned methanol charge:

| Products [kt/a] | Conventional process (MTP) | Process of the invention (MTP+) |
|---|---|---|
| Propylene | 450 (61.7%) | 477 |
| Gasoline | 214 (26.8%) | 81 |
| Aromatics | 0 | 102 |
| Others ($C_{2-}$, LPG) | 65 (8.9%) | 69 |

With the process of the invention, the production of propylene is increased by 6%. In addition, aromatics are produced as separate products, which as individual components achieve a higher sales price than the conventionally obtained gasoline product.

At the same time, the composition of the gasoline is changed as well.

| Gasoline composition [wt-%] | MTP | MTP+ |
|---|---|---|
| Olefins | 19 | 18 |
| Naphthenes | 13 | 16 |

-continued

| Gasoline composition [wt-%] | MTP | MTP+ |
|---|---|---|
| Aromatics | 46 | 4 |
| Paraffins | 12 | 62 |

The recycling stream largely free from aromatics can be converted in the reactor. In this process, however, only the olefins (conversion about 86%) and the naphthenes (conversion about 58%) are reactive, whereas the paraffins are inert. Correspondingly, it can be seen that the paraffins were greatly enriched as compared to the gasoline stream. The content of aromatics only is 4%. The paraffins therefore are discharged, and there can in particular be determined a purge content of 30%.

The substantially reduced content of aromatics increases the value of the gasoline obtained, in particular as from 2006 a maximum aromatics content of 35 wt-% is prescribed for regular gasoline inside the European Union.

LIST OF REFERENCE NUMERALS 1 reactor
2 first separating device
3 second separating device
4 methanol supply conduit
5 prereactor
6 conduit
7 steam conduit
8 conduit
9 conduit
10 compressor
11 third separating device
12 return conduit
13 conduit
14 conduit
15 conduit
16 conduit
A aromatics stream
B recycling stream

The invention claimed is:

1. A process for producing $C_2$-$C_4$ olefins from an educt mixture containing steam and oxygenates, in which the educt mixture is reacted in at least one reactor on a catalyst to obtain a reaction mixture comprising low-molecular olefins and gasoline hydrocarbons, which in a first separating device is separated into a mixture rich in $C_{5-}$ olefins, a mixture rich in $C_{5+}$ gasoline hydrocarbons, and an aqueous phase,
wherein the mixture rich in $C_{5+}$ gasoline hydrocarbons is supplied to a second separating device, in which the aromatics contained in the mixture are separated and are discharged as an aromatics stream and a separate residual stream, the separate residual stream at least partially recirculated to the at least one reactor as a recycling stream, wherein the amount of aromatics in the recycling stream recirculated to the first reactor is less than 10 wt %; and
wherein the second separating device is a membrane separating device or includes a distillation column in which an extracting agent is added.

2. The process as claimed in claim 1, wherein part of the recycling stream largely free from aromatics, which was obtained in the second separating device, is removed from the process.

3. The process as claimed in claim 1, wherein the aromatics stream separated in the second separating device is separated into benzene, toluene and a xylene-isomer mixture in a further separating device.

4. The process as claimed in claim 1, wherein the at least one reactor constitutes a shaft reactor, tubular reactor, stationary fluidized-bed reactor or circulating fluidized-bed reactor.

5. The process as claimed in claim 1, wherein two or more series-connected reactors are used or one reactor comprising at least two series-connected catalyst stages is used.

6. The process as claimed in claim 1, wherein the catalyst in the reactor is a granular, form-selective zeolite catalyst.

7. The process as claimed in claim 1, wherein the conversion in the at least one reactor is performed adiabatically.

8. The process as claimed in claim 1, wherein the first separating device is a cooling device, in which the reaction mixture is cooled to a temperature of 10 to 0° C.

9. The process as claimed in claim 1, wherein the mixture rich in $C_{5-}$ olefins, which was obtained in the first separating device, is supplied to a third separating device, in which the mixture is separated into a $C_4$-$C_5$ hydrocarbon stream, a $C_{2-}$ hydrocarbon stream and a $C_{3-}$ hydrocarbon stream.

10. The process as claimed in claim 9, wherein the $C_{2-}$ hydrocarbon stream is recirculated to the reactor.

11. The process as claimed in claim 1, wherein the mixture rich in $C_{5-}$ olefins, which was obtained in the first separating device, is supplied to a third separating device, in which the mixture is separated into a $C_4$-$C_5$ hydrocarbon stream and a $C_{3-}$ hydrocarbon stream.

12. The process as claimed in claim 9, wherein the $C_4$-$C_5$ hydrocarbon stream is recirculated to the reactor.

13. The process as claimed in claim 11, wherein propylene is separated from the $C_{3-}$ hydrocarbon stream and the remaining olefins are possibly recirculated to the reactor.

14. A plant for producing $C_2$-$C_4$ olefins from an educt mixture containing steam and oxygenates, comprising
at least one catalytic reactor for converting the educt mixture into a reaction mixture comprising low-molecular olefins and gasoline hydrocarbons, and
a first separating device for separating the reaction mixture obtained in the reactor into a mixture rich in $C_{5-}$ olefins, a mixture rich in $C5_+$ gasoline hydrocarbons, and an aqueous phase,
a second separating device which is adapted to separate the mixture rich in $C_{5+}$ gasoline hydrocarbons into a recycling stream, wherein the recycling stream is less than 10 wt % aromatics, and an aromatics stream containing the separated aromatics, and
a return conduit which leads from the second separating device to the reactor,
wherein the second separating device is a membrane separating device.

15. The plant as claimed in claim 14, wherein the catalyst in the reactor is an alumosilicate zeolite of the pentasil type.

16. The plant as claimed in claim 14, further comprising a third separating device provided downstream of the first separating device, which comprises at least one distillation column.

17. The plant as claimed in claim 16, further comprising a return conduit leading from the third separating device to the reactor.

18. A plant for producing $C_2$-$C_4$ olefins from an educt mixture containing steam and oxygenates, comprising
at least one catalytic reactor for converting the educt mixture into a reaction mixture comprising low-molecular olefins and gasoline hydrocarbons, and a first separating device for separating the reaction mixture obtained in the reactor into a mixture rich in $C_{5-}$ olefins, a mixture rich in $C_{5+}$ gasoline hydrocarbons, and an aqueous phase, a second separating device, which is a membrane separating device or includes a distillation column in which an extracting agent is added and which is adapted to separate the mixture rich in $C_{5+}$ gasoline hydrocarbons into a recycling stream, wherein the recycling stream is less than 10 weight % aromatics, and an aromatics stream (A) containing the separated aromatics, and a return conduit which leads from the second separating device to the reactor (1), wherein the second separating device includes a distillation column in which an extracting agent is added.

* * * * *